United States Patent [19]

Leonhardt

[11] Patent Number: 5,370,618

[45] Date of Patent: Dec. 6, 1994

[54] PULMONARY ARTERY POLYURETHANE BALLOON CATHETER

[75] Inventor: Howard J. Leonhardt, Davie, Fla.

[73] Assignee: World Medical Manufacturing Corporation, Fla.

[21] Appl. No.: 979,248

[22] Filed: Nov. 20, 1992

[51] Int. Cl.$^5$ .............................. A61M 29/00
[52] U.S. Cl. ................................... 604/103; 604/96; 606/192
[58] Field of Search ............... 604/96, 103, 271, 100; 606/192, 194

[56] References Cited

U.S. PATENT DOCUMENTS

| | | | |
|---|---|---|---|
| 3,833,004 | 9/1974 | Vazquez et al. | 604/100 |
| 4,675,361 | 6/1987 | Ward, Jr. | 528/92 |
| 4,913,701 | 4/1990 | Tower | 604/103 |
| 4,917,667 | 4/1990 | Jackson | 604/96 |
| 4,919,133 | 4/1990 | Chiang | 606/159 |
| 5,021,045 | 6/1991 | Buckberg et al. | 604/53 |
| 5,042,976 | 8/1991 | Ishitsu et al. | 604/96 |

Primary Examiner—C. Fred Rosenbaum
Assistant Examiner—Corrine Maglione
Attorney, Agent, or Firm—John M. Brandt

[57] ABSTRACT

A self centering, low profile, low inflation pressure pulmonary artery polyurethane balloon catheter having a reduced neck section and a balloon disposed within the neck section such that the balloon is flush with the catheter body in the deflated state and extends beyond the distal end of the catheter in both its inflated and deflated states.

5 Claims, 1 Drawing Sheet

PULMONARY ARTERY POLYURETHANE BALLOON CATHETER

BACKGROUND OF THE INVENTION

1. Field of the Invention

The invention resides in the field of pulmonary artery balloon catheters and more particularly relates to low inflation pressure, low deflated profile, self centering polyurethane devices.

2. Description of the Prior Art

Pulmonary artery balloon catheters for measuring pressures within the vascular system are well known devices in the medical field. Their primary purpose is, after insertion into the body of the patient, to provide a means for performing such measurements by inflating the balloon attached to the catheter tip. This is accomplished, for example, by the introduction of fluid into the balloon through the catheter by a syringe located externally to the patient. These catheters are intended to be left within the body for an extended period of time and therefore their construction as well as their maneuverability, manipulation, and activation with minimum danger to the patient are of great concern.

The primary material for manufacturing these balloons heretofore has been latex. There are a number of drawbacks to the use of latex which are alleviated entirely or in part by the employment of polyurethane in accordance with applicants invention. Among these drawbacks are the following.

Inflation of latex balloons is erratic due to the high tension of the material compared to polyurethane. This results in a surge to full size when the critical inflation pressure is reached as well as a tendency to inflate non uniformly or out of round nearest the catheter inflation port.

As a natural material, latex varies from lot to lot, decomposes or spoils easily and is difficult to extrude with even wall thickness.

Mechanically, it is not as durable as polyurethane, fragments when it bursts, diffuses filling gases quickly and absorbs bodily fluids. Further latex has a rougher surface making balloons composed of that material more difficult to introduce into the body and more likely to promote blood clots upon long periods of indwell.

Additionally latex has undesirable toxins and pollutants from its source and processing and can cause severe allergic reactions in some patients.

Finally it is not as easily mounted on a catheter requiring adhesives and metal bands which may be avoided with polyurethane by using solvents.

The use of polyurethane as a catheter balloon material has however been disclosed in the prior art. For example U.S. Pat. No. 4,913,701 Tower, describes a polyethylene catheter employing a thermoset polyurethane balloon attached by cuffs and an appropriate adhesive. The references contained therein particularly U.S. Pat. No. 4,661,095, Taller et al. further disclose various aspects of the technology involved in this endeavor.

Applicant has now discovered that by constructing such catheters and balloons of a particular material in a particular way, a superior device can be created which overcomes many of the deficiencies of those comprised of latex and those comprised of polyurethane as has been previously disclosed.

SUMMARY OF THE INVENTION

The invention may be summarized as a low deflated profile, low inflation pressure, self centering polyurethane balloon catheter. The balloon is comprised of substantially 80A durometer 0.004 inch wall thickness material and is preferably formed by blow molding in a bell shaped mold to achieve a device of particular elasticity which behaves upon inflation and deflation in a specific and desirable manner.

In contrast to the prior art, the catheter balloon of the invention obtained by the unique method of manufacturing disclosed herein provides a number of features and advantages constituting a significant advance in the field of pulmonary artery pressure measurements. For example the design and method of construction of the balloon provides a catheter which self centers in the artery under blood flow upon inflation. This results from an initial low inflation pressure characteristic which fills the balloon uniformly to an unstretched state followed by an additional application of inflation pressure which expands and stretches the balloon to the desired diameter and shape. Additionally the design and method of construction produce a rapidly obtained low deflated profile upon the release of inflation pressure without the necessity of drawing a vacuum, a result of the inherent elastic memory of the device. Further, by the use of a solvent to smoothly join the catheter and balloon rather than the mechanical or adhesive bonds of previous devices, the opportunity for blood clotting is greatly reduced. This is a particularly desirable aspect of the invention as these types of catheters normally dwell within the patient for a number of days.

Additional features which enhance the effectiveness and reliability of the invention include the use of epoxy for balloon-catheter joint reinforcement, and the arrangement of the balloon to cover the catheter tip when deflated.

The balloon is preferably made by introducing extruded 70A to 95A durometer polyurethane tubing into a clear acrylic or glass mold with a bell shaped cavity. The mold is dipped into hot water, and stabilized at about 165 degrees F. for about 35 seconds. One end of the tubing which is in the mold is plugged. The other end of the tubing which is outside of the mold is attached to a syringe. When the mold has been in the hot water for the required time, pressure is exerted into the tubing by advancing the plunger of the syringe filled with air. The tubing expands due to the air pressure to fill the shape of the cavity. The action of the tubing expanding to fill the cavity can be visually seen through the clear walls of the mold. When formation of the balloon is finished, the clear balloon material most often turns white for a second and then back to clear.

The mold is pulled from the hot water and dipped into cold water preferably within about two seconds of witnessing the extruded material filling the cavity. The plunger of the syringe is withdrawn collapsing the balloon allowing removal from the mold. Excess tubing material is trimmed and the proximal end of the balloon attached to the catheter by an appropriate solvent. The distal end is then everted over or reversed onto the catheter shaft below the proximal end and again attached with solvent complete the integration of the balloon and catheter. Everting provides a means for the balloon to cover the catheter tip on deflation. It is not necessary to obtain the other characteristics of the invention.

DESCRIPTION OF THE PREFERRED EMBODIMENT

Figure 1:
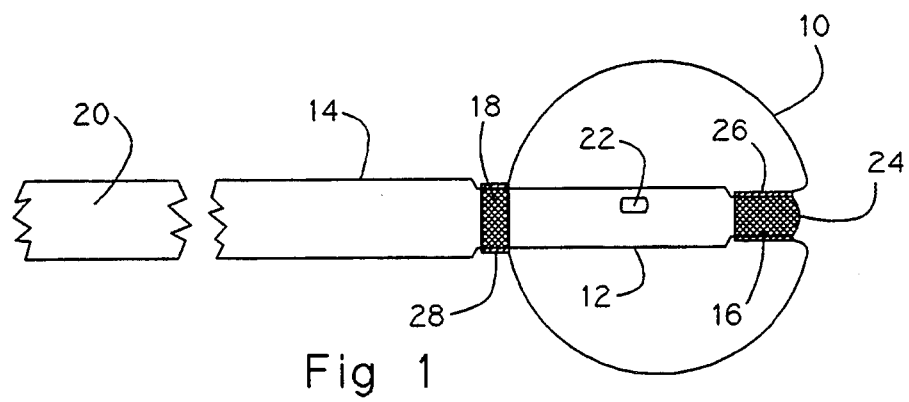
FIG. 1 is a cross sectional view of the balloon in the inflated state which comprises the preferred embodiment of the invention.
Figure 1A:
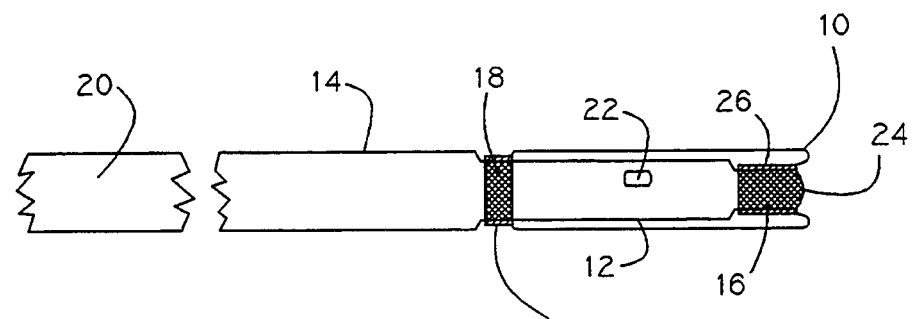
FIG. 1a is a cross sectional view of the balloon of FIG. 1 in the deflated state.

Referring to FIG. 1, there is illustrated a catheter balloon in the inflated state comprising the preferred embodiment of the invention. Balloon 10 comprised of 70A to 95A durometer polyurethane of 0.004 inch wall thickness is disposed in neck section 12 formed at the distal end of polyurethane catheter 14. It is attached so as to be fluid tight at sections 16 and 18 and is preferably secured by the application of a solvent, cylcohexanone for example. Inflation and deflation is accomplished by the introduction or withdrawal of fluid at the proximal end 20 of catheter 14 connecting with port 22 in the catheter wall. As shown in FIG. 1 balloon 10 extends at its greatest inflated distal extremety beyond neck section 12. Pressure is measured through the catheter by way of tip port 24 which is separated from the balloon inflation channels by a multi lumen interior structure not shown but as is well known to those skilled in the art. Catheter balloon interfaces 16 and 18 may further be reinforced by the application of rings of epoxy 26 and 28 which serves to streamline the surface reducing the risk of blood clots and facilitating the introduction and removal of the entire device into the cardiovascular system of the patient. For the same purpose, the balloon is also mounted in a manner to provide for the tip of the catheter to be covered upon deflation as shown in FIG. 1a.

The specified elasticity (durometer) and wall thickness of the polyurethane directly result in the features and advantages of the invention described above. Although the balloon may be constructed in various ways a preferred method of construction as will be described below utilizing a mold has been found to yield a superior and reproducable device.

Figure 2:
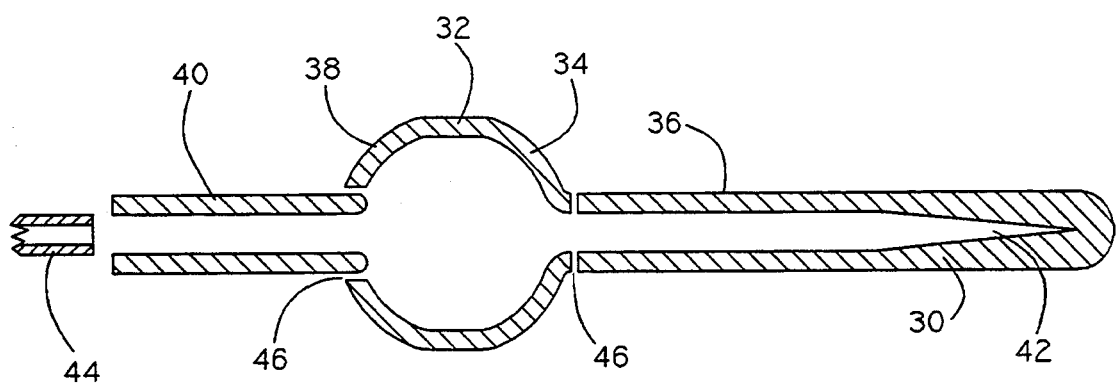
FIG. 2 is a cross sectional view of a mold used to construct the preferred embodiment of the invention.

Referring to FIG. 2, there is shown a cross sectional view of a mold particularly suited for the manufacture of the invention. Mold 30 is preferably composed of a clear material such a glass or acrylic.

It is cylindrical having a central portion 32 of greater diameter than each end portion and as shown such portion may be described as bell shaped, that is, the cross sectional slope 34 of the forward part 36 is less steep than cross sectional slope 38 of the rearward portion 40.

Forward part 36 provides an end seal 42 and for that purpose is internally tapered to produce a wedge fit upon the insertion of a polyurethane tubing work piece 44. Holes 46 provide for the escape of air when the mold is filled by the expanding workpiece.

A preferred method of construction of the balloon and catheter comprising the invention using the above described mold is as follows:

Extruded 80A durometer semi-elastic polyether, segrented, thermoplastic polyurethane tubing with a wall thickness of about 0.004" and an inside diameter appropriate to fit tightly over a catheter shaft is inserted into a glass mold with a bell shaped bulb in the center as is described above and is 15 percent smaller in diameter than the intended final inflated balloon size i.e. 10–13 mm. The bell shape of the mold is advantageous to reduce the amount of excess balloon material to provide the lowest deflated profile. The upper half of the mold is cylindrical in shape with a hole in the center with an inner diameter just large enough to freely accept the introduction of the polyurethane tubing. The bottom half of the mold is tapered so that the polyurethane tubing may be friction fitted and sealed at the bottom portion of the mold which is closed at the end. The polyurethane tubing is attached to a rigid tube with a diameter 20 percent larger than the polyurethane tubing by stretching the tubing over the rigid tube and melting or solvent bonding the polyurethane tubing to the rigid tube so that a seal is formed. The other side of the rigid tube has a luer lock connector so that a syringe with a pressure gauge may be attached. The syringe should have a volume at least equal to that of the intended end balloon inflation volume. After the syringe is attached to the rigid tube and the polyurethane tubing to the glass bulb mold and a seal is verified, the bell shaped glass bulb is immersed in a temperature controlled water bath of about 160 degrees F. to 168 degrees F. The mold is immersed just past the bulb in the mold. The bulb is left in the hot water for about 30 to, 35 seconds, after which the syringe plunger is gradually advanced to expand the tubing. While pressure is increased with the syringe the tubing is constantly pulled back in a gentle manner. This removes slack from the tubing which when the tubing blows to fill the mold, would be pulled into the bulb and otherwise cause a mis-formed balloon. During about the last 10 percent of the depression of the syringe the polyurethane tubing will expand to fill the shape of the glass bulb. After the tubing is blown into the shape of the bulb more pressure is exerted to completely fill the corners of the mold and set the balloon shape. The mold is removed from the hot water bath and set in a cold water bath of about 40 degrees F. while the balloon is still inflated. After about 5 seconds, the syringe plunger is withdrawn to pull the tubing off the walls of the bulb and to pull the rigid tube away from the mold to remove the polyurethane tubing including the blown balloon bulb center from the mold. The bottom portion of the polyurethane tubing is pinched with a hemostat for example to seal the end and to allow inflation of the balloon in the air to test for symmetry and shape.

Unexpanded portions of tubing above and below balloon are cut, allowing a 2 mm section on each end for mounting purposes, The polyurethane material catheter is prepared by tapering the tip in two parts using a heated mold. The first taper, just long enough to accomodate the portion of the tubing to be bonded to the catheter, about 2 mm, is greater than the second longer taper, about 7 mm. The bottom portion of the balloon is then mounted on the top taper of the catheter by stretching the tubing of the balloon into place over the extra tapered 2 mm segment. When in place the solvent cylcohexanone is wiped onto the 2 mm segment using an ordinary nylon paint brush, avoiding contact with the blown balloon itself. A pair of heated crimping pliers may be used to crimp seal the 2 mm segment onto the catheter in addition to the chemical bonding. The balloon-catheter is then set aside for about 10 minutes to allow the chemical bond reaction created by the cylcohexanone. After this, the balloon is flipped over itself or everted creating a cone over the catheter tip and setting in place the second 2 mm segment of balloon tubing to be mounted onto the bottom portion of the polyurethane catheter tip tapered portion. This segment is bonded as the first by painting cyclohexanone on the segment to create a chemical bond between the polyurethane balloon tubing segment and the polyurethane catheter tapered portion. Again, a pair of heated crimping pliers may be used to reinforce the strength of the bond by melting the balloon tubing segment into the polyurethane catheter material. After allowing this segment to set for 10 minutes, epoxy bands are painted for example Isoproplidenediphenol epichlorohyrin based epoxy and/or similar isomers around the sections of the balloon tubing that were chemically bonded to the catheter. This serves the purpose of smoothing out the transition of the balloon to the catheter to reduce the chance of causing a stagnation point in the flow of blood. It also serves a second purpose of reinforcing the balloon to catheter bond and smoothing out the tip portion of the catheter to avoid scraping the inside of the blood vessel walls.

What is claimed is:

1. A pulmonary artery balloon catheter for wedge pressure measurements comprising in combination:
   1. A tubular catheter body formed of polyurethane adapted for insertion into the cardiovascular system said body having a distal end and a proximal end, said body having a reduced neck section at the distal end said neck section having a proximal and a distal end and further having a port in said neck section connecting with the interior of said body, said neck section terminating in a rounded configuration; and
   2. An inflatable balloon having a proximal and distal end disposed within said neck section over said port arranged to be flush with said catheter body in its deflated state, said balloon comprised of polyurethane of substantially 70A to 95A durometer and of a wall thickness of substantially 0.004 inches, said balloon arranged to inflate to a diameter of from 10 to 13 millimeters, said balloon arranged to extend at its greatest distal extremity beyond said distal end of said neck section in both its inflated and deflated states.

2. The apparatus of claim 1 wherein said balloon is comprised of extruded polyurethane.

3. The apparatus of claim 1 wherein said balloon is bonded to said catheter body by a solvent 4. The apparatus of claim 3 wherein said solvent comprises cyIcohexanone.

5. The apparatus of claim 3 further including a ring of epoxy disposed at the bonded juncture of said balloon and said catheter

* * * * *